(12) United States Patent
Ross, III et al.

(10) Patent No.: US 7,244,026 B1
(45) Date of Patent: Jul. 17, 2007

(54) STERILIZABLE OPHTHALMOSCOPY LENS SYSTEM

(75) Inventors: Denwood F. Ross, III, Austinburg, OH (US); Tim D. Edwards, Cleveland, OH (US); C. Thomas Marek, Findlay, OH (US)

(73) Assignee: Volk Optical, Inc., Mentor, OH (US)

( * ) Notice: Subject to any disclaimer, the term of this patent is extended or adjusted under 35 U.S.C. 154(b) by 471 days.

(21) Appl. No.: 10/689,568

(22) Filed: Oct. 20, 2003

Related U.S. Application Data

(60) Provisional application No. 60/419,799, filed on Oct. 19, 2002, provisional application No. 60/419,452, filed on Oct. 18, 2002.

(51) Int. Cl.
*A61B 3/00* (2006.01)

(52) U.S. Cl. ................................. 351/219; 351/205

(58) Field of Classification Search ......... 351/200–247
See application file for complete search history.

(56) References Cited

U.S. PATENT DOCUMENTS

| | | | |
|---|---|---|---|
| 4,627,694 A | 12/1986 | Volk | |
| 4,682,866 A | 7/1987 | Volk | |
| 4,721,378 A | 1/1988 | Volk | |
| 4,738,521 A | 4/1988 | Volk | |
| 4,913,545 A | 4/1990 | Volk | |
| 5,046,836 A | 9/1991 | Volk | |
| 5,200,773 A | 4/1993 | Volk | |
| 5,255,025 A | 10/1993 | Volk | |
| 5,333,017 A | 7/1994 | Volk | |
| 5,430,506 A | 7/1995 | Volk | |
| 5,436,680 A | 7/1995 | Volk | |
| 5,479,222 A * | 12/1995 | Volk | ........................... 351/219 |
| 5,523,810 A | 6/1996 | Volk | |
| 5,526,074 A | 6/1996 | Volk | |
| 5,706,073 A | 1/1998 | Volk | |
| 5,745,212 A | 4/1998 | Volk | |
| 5,757,464 A | 5/1998 | Volk | |
| 5,784,147 A | 7/1998 | Volk | |
| 5,805,269 A | 9/1998 | Volk | |
| 5,886,812 A | 3/1999 | Volk | |
| 6,019,472 A * | 2/2000 | Koester et al. | ............. 351/219 |
| 6,142,630 A * | 11/2000 | Koester | ...................... 351/219 |
| 6,164,779 A * | 12/2000 | Volk | ........................... 351/219 |
| RE37,298 E | 7/2001 | Volk | |
| 7,144,111 B1 * | 12/2006 | Ross et al. | ................... 351/219 |

* cited by examiner

*Primary Examiner*—Huy Mai
(74) *Attorney, Agent, or Firm*—Dinsmore & Shohl LLP

(57) ABSTRACT

An autoclavable and sterilent-resistant ophthalmoscopy lens system having a plastic contact lens, and at least one image forming lens element. An ophthalmoscopy lens system having a contact lens element, an image forming lens and a retaining ring is also provided.

5 Claims, 9 Drawing Sheets

STERILIZABLE OPHTHALMOSCOPY LENS SYSTEM

This application claims the benefit of U.S. Provisional Application Ser. Nos. 60/419,452 filed on Oct. 18, 2002 and 60/419,799 filed on Oct. 19, 2002, the entire disclosures of which are hereby incorporated herein by reference.

BACKGROUND OF THE INVENTION

1. Field of the Invention

The present invention relates to ophthalmoscopy lens systems, particularly those which may be sterilized without component damage or optical degradation.

2. Description of Related Art

Various ophthalmoscopy lens systems have been developed for use in the diagnosis and treatment of the eye. Many of these lens systems, particularly indirect ophthalmoscopy lens systems which create a real aerial image of structures within the eye, include a contact lens element which is placed directly on a patient's cornea. One particular type of indirect ophthalmoscopy lens systems is that used for vitreoretinal surgery. Such lens systems are described, for example, in U.S. Pat. No. 5,963,301 (which is incorporated herein by way of reference). Such lens systems are typically exposed to various bodily fluids during use, and therefore must be sterilized prior to each use.

Sterilization of ophthalmoscopy lens systems can be difficult and time consuming. In fact, many ophthalmoscopy lens systems can only be sterilized by specialized, time-consuming sterilization techniques, many of which will not be effective for certain microorganisms and other infectious agents. By way of example, "prions" are proteinaceous infectious agents which can cause transmissible degenerative encephalopathies such as Creutzfeldt-Jakob disease ("CJD"—a variant of which is the human version of "Mad Cow disease"). Prions tend to be more resistant to steam sterilization than conventional agents and are resistant to most sterilants typically used for sterilizing ophthalmoscopy lens systems. Recently, it has been reported that prions are susceptible to conventional autoclaving followed by a strong bleach solution or a solution of sodium hydroxide. Such a sterilization process will denature the prions. However, this technique cannot be employed with conventional ophthalmoscopy lens systems, particularly vitreoretinal lens systems such as those described in U.S. Pat. No. 5,963,301. Not only will the bleach solution damage the plastic contact lens element and other components, liquid will enter the air space between the contact lens element and the imaging lens.

In the past, various techniques have been used in an attempt to seal ophthalmoscopy lens systems. For example, various types of glue and other sealants have been positioned between lens elements and the frame. However, glues will eventually decompose and will never fully seal a lens assembly, thereby resulting in condensation on the interior of the lens which renders the lens system useless. Autoclaving will also cause degradation of glues.

Although some prior art ophthalmoscopy lens systems comprising a contact lens element and one or more imaging lens elements can be dissembled for sterilization purposes, some of the materials used in manufacturing the various elements of such lens systems are such that they must be sterilized using ethylene oxide. Such a sterilization process can take many hours to complete, and is much more expensive than other sterilants such as bleach. Sterilizing lens systems using a bleach solution (such as sodium hypochlorite), even if preceded by autoclaving, is much faster than sterilization using ethylene oxide. The time for sterilization can be further decreased if the ophthalmoscopy lens systems does not need to be disassembled prior to sterilization. Disassembling the lens prior to sterilization is time-consuming, and it is difficult to ensure that all moisture has been eliminated from the lens system upon re-assembly.

SUMMARY OF THE INVENTION

The present invention provides an autoclavable and sterilent-resistant ophthalmoscopy lens system, comprising a plastic contact lens, and at least one image forming lens element. Such a lens system may be used, for example, as an indirect ophthalmoscopy lens system for use in the diagnosis or treatment of a patient's eye (e.g., laser treatment). In one particular embodiment, the lens system is configured such that the contact lens and the at least one image forming lens element are in a spaced-apart sealed arrangement such that a sealed air space is provided between the contact lens and the at least one image forming lens element. Of course more than one image forming lens elements may be employed, and a compound contact lens may be used if desired.

In one particular embodiment, the ophthalmoscopy lens system further comprises a housing, wherein the contact lens and the at least one image forming lens element are sealingly mounted to the housing. For example, the housing may have posterior and anterior ends, with the contact lens threadingly mounted to the housing at the posterior end of the housing. The image forming lens may be positioned at least partially (or entirely) within the housing, and a sealing member may be located between the image forming lens and the interior of said housing in order to provide a sealed lens system. Likewise, a sealing member may be positioned between the contact lens and the housing. A threaded retaining ring configured for retaining the image forming lens at least partially within said housing may also be provided. Any of a variety of sealing members may be employed, however, they should be autoclavable and sterilent-resistant in order to maintain the sealing of the lens system after sterilizing and autoclaving. For example, an O-ring or gasket made of a suitable material may be used. Alternatively, the sealing member may comprise a sealant composition which is autoclavable and sterilent-resistant, particularly a curable sealant composition which forms a flexible seal. A second sealing member may be positioned between the image forming lens and the interior of said housing in order to provide additional sealing of the air space between the contact lens and the image forming lens element.

In order to further prevent moisture within the air space located between the contact lens and the image forming lens element, a desiccant may be positioned within the housing between the contact lens and the image forming lens element. For example, the housing may include a flat wall portion adjacent the air space and a desiccant may be adhesively applied to this wall. Suitable desiccants include any substance(s) which has a high affinity for water, such as calcium oxide, calcium sulfate or silica gel.

In an alternative embodiment, the lens system is configured such that there is no air space between the contact lens and the at least one image forming lens element. The contact lens and the image forming lens may include mating surfaces having substantially the same shape such that they be essentially be positioned in contact with one another with a thin fluid layer (such as saline) located therebetween. In this embodiment, the lens system may include a retaining ring configured to maintain the contact lens element and the image forming lens in optical alignment with a fluid layer positioned therebetween. The retaining ring may comprise an annular ring configured such that the retaining ring extends around the outer circumference of the image forming lens. For example, the image forming lens may be held within a circular groove in the retaining ring, particularly when the retaining ring is manufactured from a resilient material. The retaining ring may also be configured to engage the contact lens element so as to maintain the contact lens element and the image forming lens in a mating, optically-aligned relationship.

Another embodiment of the present invention provides an ophthalmoscopy lens system having at least first and second lens elements, wherein the first and second lens elements are mounted in a spaced-apart sealed arrangement such that a sealed air space is provided between the lens elements. The lens system is configured such that it may be immersed in a fluid without the fluid entering said sealed air space. In an exemplary embodiment, the first lens element may comprise a contact lens element and the second lens element may comprise an image forming lens element. This lens system may also include a housing, wherein the contact lens and the at least one image forming lens element are sealingly mounted to the housing.

Yet another embodiment of the present invention provides an ophthalmoscopy lens system comprising a contact lens element, an image forming lens and a retaining ring. The contact lens element has a posterior lens surface with a concave shape substantially corresponding to the shape of an average cornea, and an anterior surface. The image forming lens has anterior and posterior surfaces, wherein the anterior surface has a shape corresponding to the shape of the anterior surface of the contact lens element. The retaining ring may be configured to maintain the contact lens element and the image forming lens in mating relationship with one another. In one embodiment, the contact lens element and image forming lens are maintained in mating relationship with one another without an air space therebetween, and may include a fluid layer therebetween.

The retaining ring in this embodiment may comprise an annular ring configured such that the retaining ring extends around the outer circumference of the image forming lens. The retaining ring may also be configured to engage the contact lens element so as to maintain the contact lens element and the image forming lens in their mating relationship. The retaining ring may include a groove extending about the interior circumference of the retaining ring, and the contact lens element may include a plurality of mounting tabs configured to be positioned within the groove for maintaining the contact lens element and the image forming lens in their mating relationship. In one embodiment, the anterior surface of the contact lens element may be concave, and the image forming lens may be biconvex.

BRIEF DESCRIPTION OF THE DRAWINGS

While the specification concludes with claims particularly pointing out and distinctly claiming the present invention, the invention will be further understood from the following detailed description taken in conjunction with the accompanying drawings in which:

DETAILED DESCRIPTION

The present invention provides an ophthalmoscopy lens system, such as a lens system suitable for use during vitreoretinal surgery, which may be easily and effectively sterilized. In particular, lens systems according to the present invention may be sterilized (or disinfected) by immersion in chemical sterilants such as glutaraldehyde, hydrogen peroxide or bleach (e.g., sodium hypochlorite). These lens systems may also be sterilized by steam sterilization (such as by use of an autoclave). By proper selection of the materials used to manufacture the various components of the lens system, the lens system can be sterilized without significant damage to the components (particularly the individual lens elements) or degradation of the optical characteristics of the lens system. Some embodiments of the present invention are sealed such that the lens need not be disassembled for sterilization purposes, while other embodiments permit the lens to be quickly and easily disassembled prior to sterilization.

Figure 1:
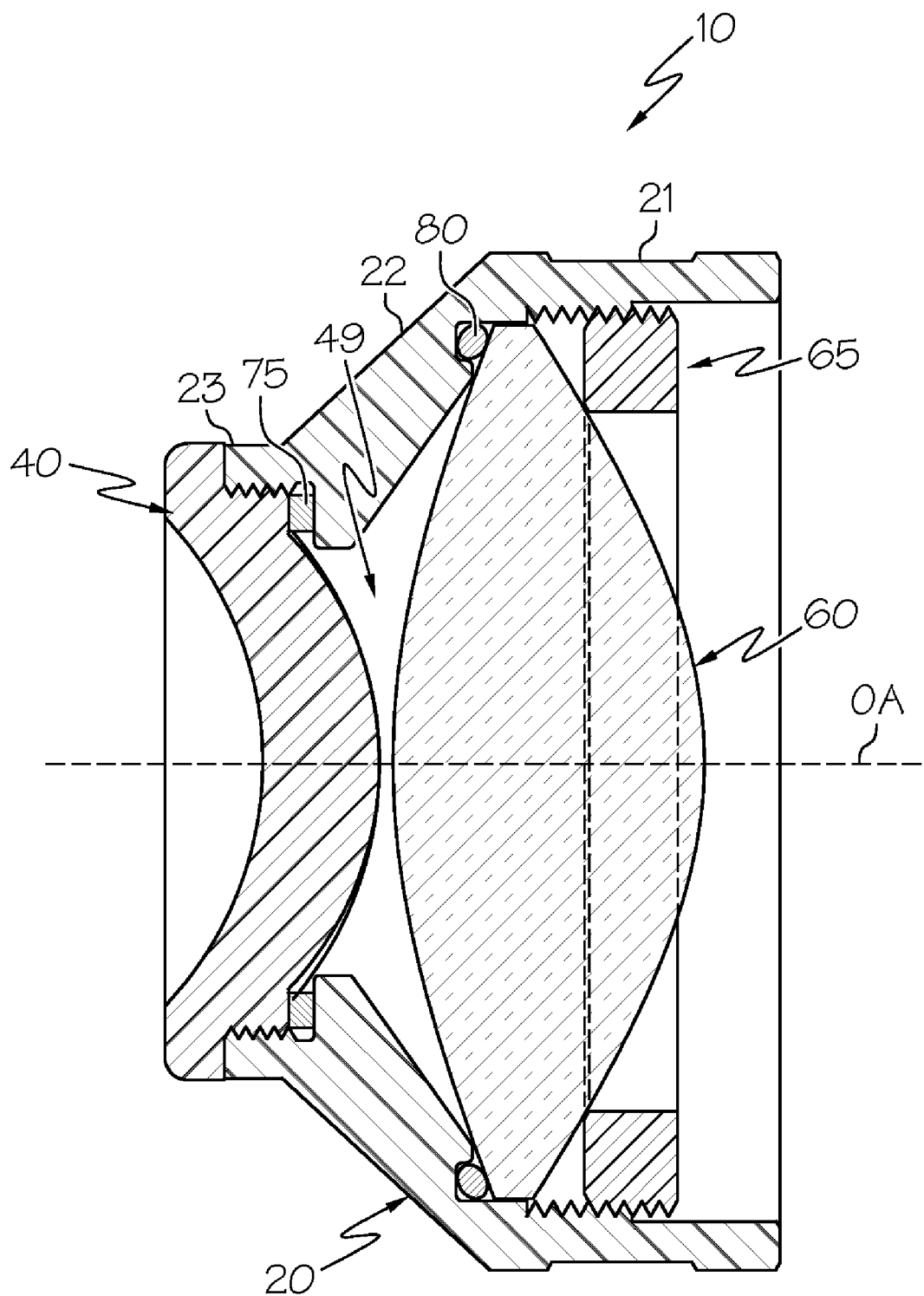
FIG. 1 is a cross-sectional view of one embodiment of a sterilizable ophthalmoscopy lens system according to the present invention.

FIG. 1 is a cross-sectional view of a vitreoretinal lens system 10 according to one embodiment of the present invention. Lens system 10 generally includes a contact lens element 40 and an image forming lens 60, both of which are mounted in a housing or frame 20. As further described herein, contact lens element 40 is threadingly secured to housing 20, while image forming lens 60 is retained within housing 20 by means of a threaded retainer ring 65. Housing 20 is configured such that contact lens element 40 and image forming lens 60 may be mounted thereto in a predetermined, precise orientation, with a sealed air space 49 provided between contact lens element 40 and image forming lens 60.

In order to ensure that air space 49 of the lens system is sealed, one or more sealing members are employed between each of the lens elements (i.e., contact lens element 40 and image forming lens 60) and frame 20. In this manner, fluid or other contaminates may not enter air space 49, particularly during sterilization. Any of a variety of sealing members may be used, such as gaskets, O-rings, or even sealant compositions applied between the lens element and frame 20. In the embodiment shown in FIG. 1, the sealing members include an O-ring 80 positioned between image forming lens 60 and frame 20, and a gasket 75 positioned between contact lens element 40 and frame 20. When sealed in this manner, lens system 10 shown in FIG. 1 may be sterilized by any of a variety of techniques (including immersion in a chemical sterilant or even steam sterilization) without the risk of liquid entering air space 49.

Besides the sealing of the lens system, another aspect of the present invention is the selection of the materials for the individual components of the lens system in order to ensure that these materials are chemically, thermally and mechanically compatible with one another, as well as being impervious to common sterilants (such as bleach). Since imaging forming lens 60 will typically be made from glass, the type of glass used should not only provided the desired optical properties but also be suitable for sterilization. In particularly, the glass should be chosen such that it may be sterilized in a solution of NaOH having a concentration of 1M NaOH and/or in a chlorine bleach solution (sodium hypochlorite) having a concentration of at least 20,000 ppm of free available chlorine (and perhaps even as high as 50,000 ppm, the equivalent of full strength household bleach). The glass should also be capable of being steam sterilized (e.g., in an autoclave) at temperatures of at least about 275° F. Of course the lens systems of the present invention may also be capable of being sterilized by other conventional means such as glutaraldehyde or hydrogen peroxide without damage. The selection of the "prescription" (or shape) of imaging forming lens 60 is well-known to those skilled in the art, and may be varied in order to provide the desired optical characteristics for lens system 10.

Figure 4:
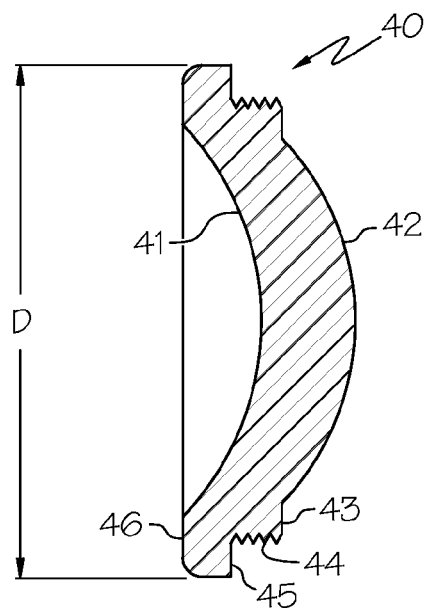
FIG. 4 is a cross-sectional view of the contact lens element employed in the sterilizable ophthalmoscopy lens system of FIG. 1.

While contact lens element 40 may also be formed from glass, optical-grade plastic will more typically be used due to its ease of manufacture and its resistance to chipping. As best seen in FIG. 4, contact lens element 40 has a concave posterior surface 41 and a convex anterior surface 42. As used herein, the term "posterior surface" refers to the surface of a lens element which is located nearer to the patient's eye during normal use. Concave posterior surface 41 has a shape substantially corresponding to the shape of an average cornea. By way of example, concave posterior surface 41 may be spherical in shape and have an apical radius of approximately 7.5 to 8.0 mm. Convex anterior surface 42 may have a similar shape, or may be varied depending on the intended use of the lens, as is well-known to those skilled in the art.

The plastic material used in the manufacture of contact lens element 40 is chosen not only for its appropriate optical properties, but also to ensure that it is chemically resistant, particularly to sterilants such as bleach (e.g., sodium hypochlorite). In one embodiment, the plastic used to manufacture contact lens element 40, as well as the other materials used in the manufacture of the lens system, should be "sterilent-resistant." As used herein, the term "sterilent-resistant" means that the component may be sterilized in a chlorine bleach solution (sodium hypochlorite) having a concentration of at least 20,000 ppm of free available chlorine (and perhaps even as high as 50,000 ppm, the equivalent of full strength household bleach), without damage which affects the performance of the component. The components may also be "autoclavable", which means that the component can be steam sterilized (e.g., in an autoclave) at temperatures of at least about 275° F. (or even 300° F.) without damage which affects the performance of the component. It is also preferable that the components may be sterilized in a solution of NaOH having a concentration of 1M NaOH without damage which affects the performance of the component.

Various sterilent-resistant and autoclavable plastics (high temperature plastics) may be used in the manufacture of contact lens element 40, particularly high temperature, chemically-resistant plastics having an index of refraction greater than about 1.4. Suitable plastics include: Ultem® 1010, an amorphous thermoplastic polyetherimide available from GE Plastics; Zeonor®, a cyclo-olefin polymer available from Zeon Corp.; Udel® P-3703 NT 05, a high temperature polysulfone available from Solvay Advanced Polymers; THV 220G, an optical-grade fluorinated terpolymer available from Dyneon; and NightShield®, a polyurethane available from Korry Electronics. During the manufacture of the contact lens element, as well as the frame and retaining ring (when made of plastic), the component should be annealed after fabrication in accordance with the annealing instructions provided by the manufacturer of the plastic.

Frame 20 and retaining ring 65 may also be made from any of a variety of materials which are sterilent-resistant. Most metals such as aluminum should be avoided, as they will corrode in a bleach solution. One particular material which may be employed is polyphenylsulfone thermoplastic resin which provides chemical resistance as well as heat resistance. Such materials are not only resistant to common sterilants (including bleach), they can also be heated to at least 275° F. without significant deformation (i.e., they are autoclavable). One particular polyphenylsulfone which may be used is medical-grade Radel®, a high performance polysulfone thermoplastic available from Solvay Advanced Polymers.

Materials used for the sealing members, such as O-ring 80 and gasket 75, should also be sterilant-resistant and autoclavable, while still having the appropriate mechanical properties to provide the necessary sealing of air space 49. Suitable materials for such sealing members include fluoroelastomers, such as Viton®, a fluoroelastomer available from DuPont Dow Elastomers.

Turning to the specific structural aspects of the exemplary embodiment depicted in FIGS. 1–5, housing 20 is hollow in nature. Housing 20 includes generally cylindrical anterior portion 21 and posterior portion 23, and a frusto-conical portion 22 located therebetween. The outer diameter of cylindrical posterior portion 23 may be less than that of anterior portion 21, and may substantially correspond to the outer diameter "D" of contact lens element 40 (see FIG. 4). Diameter D may be selected to fit a suture-down ring or other device for securing the lens to a patient's eye. Alternatively, contact lens element lens 40 may include a flange for stabilizing the lens system on the patient's eye, as described in U.S. Pat. No. 5,963,301 (which is incorporated herein by way of reference).

Figure 2:
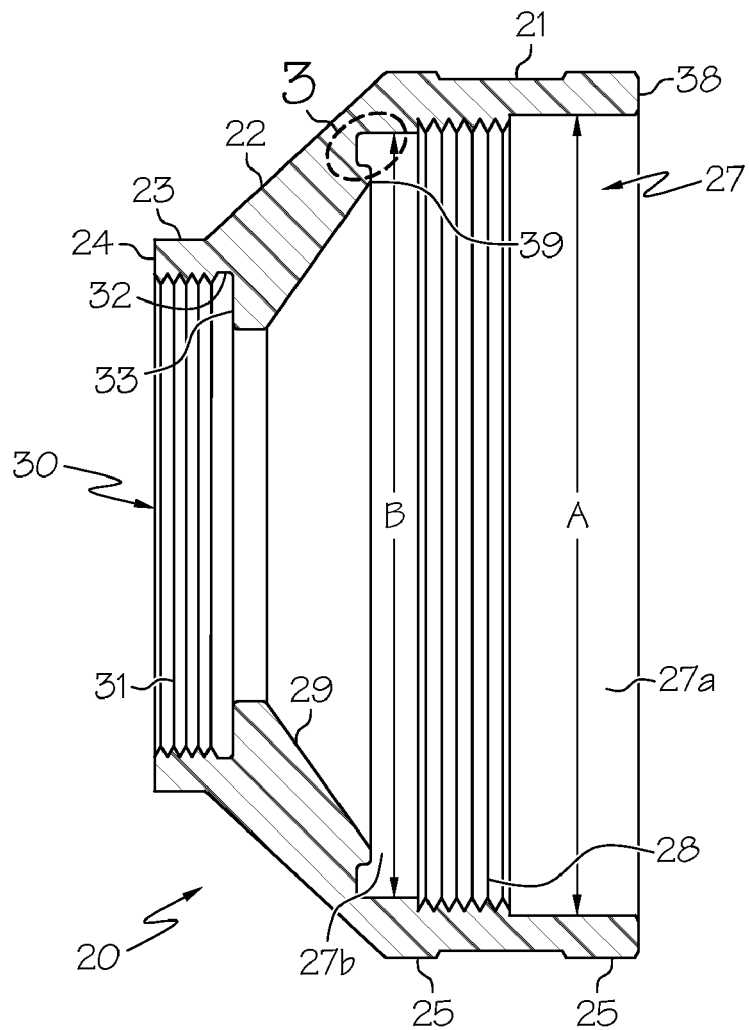
FIG. 2 is a cross-sectional view of the frame employed in the sterilizable ophthalmoscopy lens system of FIG. 1.

Cylindrical anterior portion 21 should be of a sufficient diameter to house lens element 60 therein and to facilitate handling of the lens by the practitioner If desired, one more raised portions 25 may be provided along the outer surface of frame 20, such as shown in FIG. 2. These raised portions may also be knurled or otherwise textured in order to facilitate manipulation of lens system 10 by the practitioner. As will be apparent from the figures, frusto-conical portion 22 merely provides a tapered transition between posterior portion 23 and anterior portion 21. It will also be apparent that frame 20 may generally be symmetrically configured with respect to optical axis OA (see FIG. 1).

As mentioned above, frame 20 is generally hollow in nature, such that image forming lens 60 may be positioned at least partially within frame 20 (or completely, as shown in FIG. 1). As seen in FIG. 2, the interior of the anterior portion 21 of frame 20 comprises a cylindrical bore 27 which extends inwardly away from anterior surface 38 of frame 20. In the particular embodiment shown, the sidewalls of cylindrical bore 27 may be stepped in nature such that the diameter A of the first portion 27a of cylindrical bore 27 is greater than the diameter B of second portion 27b of cylindrical bore 27. As best seen in FIG. 1, diameter B may be slightly greater than the diameter of image forming lens 60 such that, when image forming lens 60 is positioned within frame 20 in the manner shown in FIG. 1, the sidewalls of second portion 27b of cylindrical bore 27 will ensure that lens 60 is properly aligned within frame 20.

Figure 5:
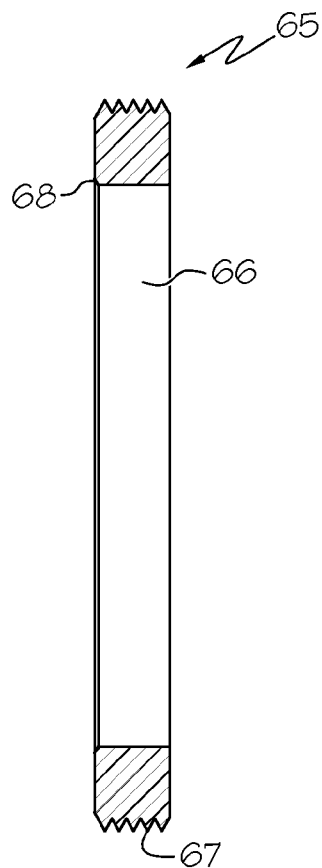
FIG. 5 is a cross-sectional view of the retaining ring employed in the sterilizable ophthalmoscopy lens system of FIG. 1.

A retaining ring 65 may be employed to retain lens 60 within housing 20, as shown in FIG. 1. In particular, at least a portion of first portion 27a of cylindrical bore 27 may be threaded. As best seen in FIG. 5, retaining ring 65 generally comprises a ring-shaped member having a central opening 66. The outer circumference of retaining ring 65 includes threads 67 configured to threadingly engage threads 28 of cylindrical bore 27 in frame 20.

Posterior edge 68 which extends about the circumference of central opening 66 may be beveled in order to correspond to the shape of the anterior surface of lens 60. In this manner, after image forming lens 60 has been positioned within frame 20 in the manner shown in FIG. 1, retaining ring 65 may be inserted into cylindrical bore 27 such that threads 67 on retaining ring 65 will threadingly engage threads 28 of frame 20. Beveled edge 68 of retaining ring 65 will be urged against the anterior surface of lens 60, thereby retaining lens 60 within frame 20, while central opening 66 of retaining ring 65 will allow light rays to pass therethrough. It should also be pointed out that, depending upon the shape of image forming lens 60, at least a portion of lens 60 may extend entirely through the thickness of central opening 66 of retaining ring 65 (as shown in FIG. 1). It should also be noted that the proximal surface of lens 10 will rest against curved edge 39 of cylindrical bore 27.

In order to assist in sealing air space 49, one or more sealing members may be provided between image forming lens 60 and frame 20. In the particular embodiment shown in FIG. 1, an O-ring 80 is employed for this purpose. It should be kept in mind, that various other sealing devices may similarly be used for this purpose, such as a gasket or other known type of sealing member.

Figure 3:
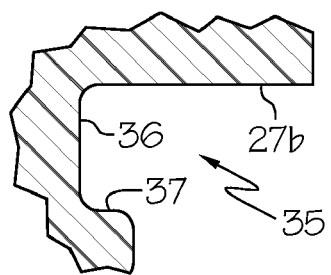
FIG. 3 is an enlarged cross-sectional view of a portion of the frame of FIG. 2.

In order to allow for proper sealing by O-ring 80, an annular groove or gland 35 may be provided at the posterior end of cylindrical bore 27 (see FIG. 3). Gland 35 should be appropriately sized and configured such that not only may an O-ring 80 be positioned therein, but also such that lens 60 may be urged against O-ring 80 by retaining ring 65 in order to deform O-ring 80 and provide the desired sealing.

As best seen in FIG. 3, gland 35 is provided by the sidewall of second portion 27b of cylindrical bore 27, bottom wall 36 which generally extends perpendicular to the optical axis of the lens, and sidewall 37 which extends away from bottom wall 36 in the anterior direction. Sidewall 37 may extend substantially parallel to the optical axes of lens 10, as shown. Gland 35 therefore essentially comprises an annular groove which extends about the circumference of the posterior end of cylindrical bore 27.

As best seen in FIG. 1, when lens 60 and retaining ring 65 are installed in frame 20, O-ring 80 will be compressed not only against the posterior surface of lens 60, but also two or more walls of gland 35.

As also seen in FIG. 2, the interior of the posterior portion 23 of frame 20 comprises a cylindrical bore 30 which extends inwardly away from posterior end 24 of frame 20. Cylindrical bore 30 is threaded such that a contact lens element 40 may be threadeningly secured to frame 20, as further described herein. Cylindrical bore also includes a flat anterior wall 33 which may extend substantially perpendicular to the optical axis of lens 10.

As described previously, contact lens element lens 40 includes a concave posterior surface 41 and a convex anterior surface 42. In order to facilitate positioning of lens 10 within a suture-down ring or other holding device, an annular surface 46 extends about the circumference of concave posterior surface 41 of contact lens element 40. In this manner, contact lens element 40 will have a sufficient diameter D to enable its use with a suture-down ring without altering or effecting the shape of concave posterior surface 41. Annular surface 46 will also facilitate the installation and removal of contact lens element 40 from frame 20 without contacting concave posterior surface 41 (which may result in smudging or damage to this surface).

Threads 44 extend about the circumference of contact lens element 40 and are located posterior to convex anterior surface 42. Threads 44 are spaced inwardly with respect to annular surface 46 such that the diameter of threads 44 is less than that of outer diameter D of contact lens element 40. In this manner, a flat surface 45 will be provided adjacent to threads 44 such that, when contact lens element 40 is threaded onto frame 20, flat surface 45 will engage the posterior end surface 24 of frame 20 (as seen in FIG. 1). The engagement between surface 45 and posterior end surface 24 of frame 20 also serves to define the positioning of contact lens 40 in frame 20. In other words, contact lens 40 may be threaded onto frame 20 until the engagement of surface 45 with posterior end surface 24 frame 20 limits further penetration of contact lens element 40 into frame 20. This ensures that the desired spacing between contact lens element 40 and image forming lens 60 is maintained.

A flat, annular surface 43 also extends about the periphery of convex anterior surface 42 of contact lens element 40, as shown in FIG. 4. Annular surface 43 may be configured such that, when contact lens element 40 is threadingly engaged onto frame 20, annular surface 43 will be substantially parallel to annular flat surface 33 of cylindrical bore 30 of frame 20. In this manner, a sealing member, such as a gasket 75, may be positioned between flat annular surfaces 43 and 33. The sealing member will be compressed between these two surfaces when contact lens element 40 is threaded onto frame 20 in the manner shown in FIG. 1. In the embodiment shown, gasket 75 has a generally rectangular cross-sectional shape. One advantage of employing a flat gasket compressed between adjacent flat surfaces of contact lens member 40 and frame 20 is that, not only will gasket 75 provide the desired sealing of air space 49, the increased area of contact between gasket 75 and contact lens element 40 will provide a frictional force which prevents contact lens element 40 from backing out of threaded engagement with frame 20. Furthermore, as is the case with O-ring 80, the compressible nature of gasket 75 will provide back-pressure on the threads, further preventing the contact lens element and the retaining ring from backing out of threaded engagement with frame 20.

The above-described lens may be sterilized in any of a variety of manners. For example, the lens assembly can be totally submersed in a liquid sterilant without risk of the sterilant leaking into air space 49. The lens assembly may also be sterilized in a steam environment at temperatures of at least 275° F. without water vapor leaking into air space 49. Thus, lens systems according to the present invention may be quickly and easily sterilized by any of a variety of methods.

Of course, it is also possible to remove contact lens element 40 from lens system 10, if desired. While removal of contact lens element 40 will obviously eliminate any concern with respect to the sealing of air space 49, the materials chosen for the various components of the lens systems of the present invention do provide significant improvements over prior art lens systems in that these materials may be sterilized by any of a variety of conventional means (such as immersion in a liquid sterilant such as bleach or autoclaving). In fact, an alternative embodiment of the present invention does not employ a gasket 75 and/or an O-ring 80 in those instances where the practitioner desires to remove contact lens element 40 for sterilization purposes. In such embodiments, contact lens element 40 and/or image forming lens 60 may be configured so as to engage frame 20 in any of a variety of conventional manners well-known to those skilled in the art.

Figure 6:
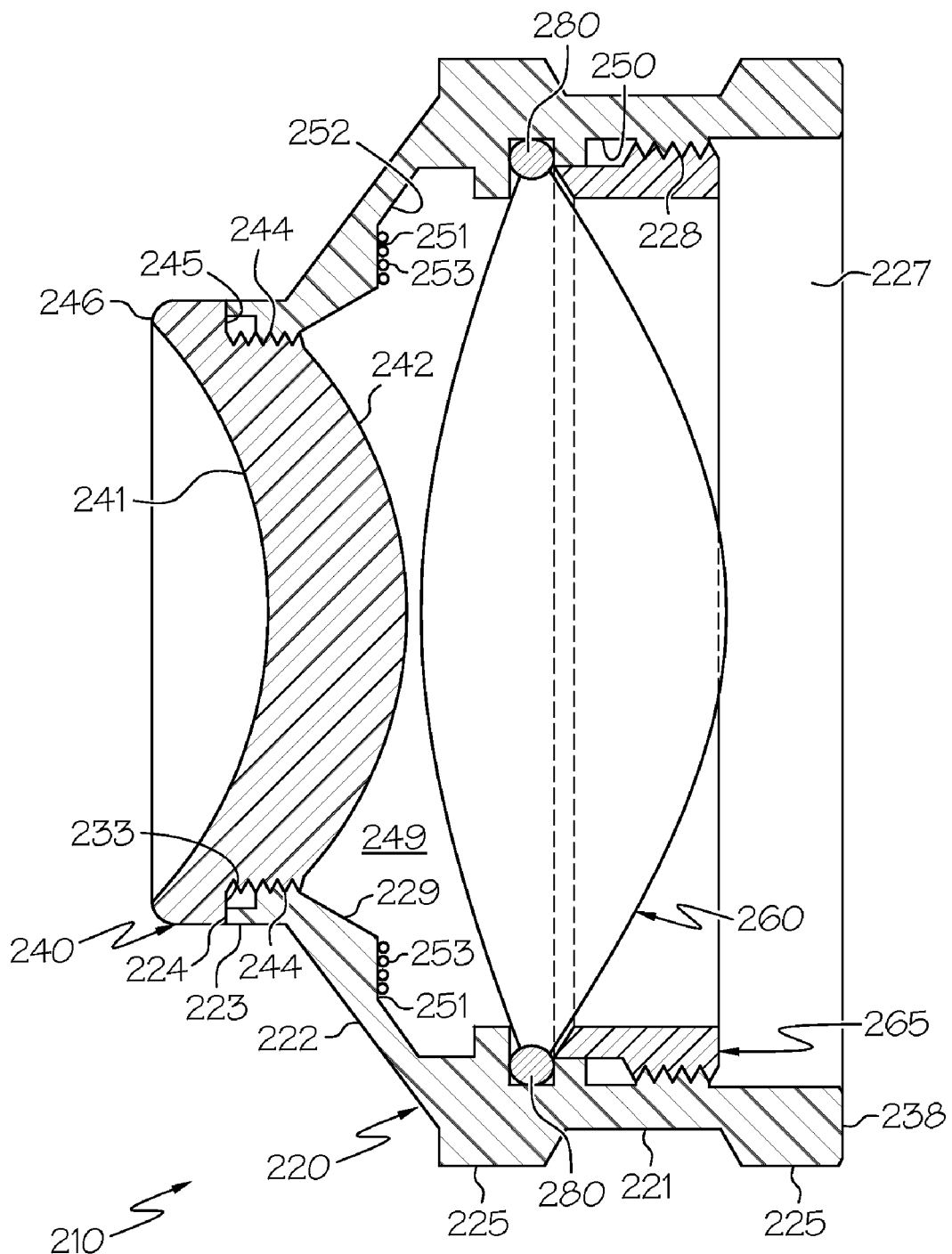
FIG. 6 is a cross-sectional view of another embodiment of a sterilizable ophthalmoscopy lens system according to the present invention.

FIG. 6 depicts an alternative embodiment for a sterilizable ophthalmoscopy lens system. In the embodiment shown in FIG. 6, lens system 210 generally comprises a housing (or frame) 220 having generally cylindrical anterior portion 221 and posterior portion 223, and a frusto-conical portion 222 located therebetween. As before, the outer diameter of cylindrical posterior portion 223 may be less than that of anterior portion 221, and may substantially correspond to the outer diameter of a contact lens element 240.

Cylindrical anterior portion 221 should be of a sufficient diameter to house a lens element 260 therein and to facilitate handling of the lens by a practitioner. If desired, one or more raised portions 225 may be provided along the outer surface of housing 220. These raised portions may also be knurled or otherwise textured in order to facilitate manipulation of lens system 210 by a practitioner.

As was the case with the embodiment of FIGS. 1–5, housing or frame 220 is generally hollow in nature such that an image forming lens 260 may be positioned at least partially within frame 220 (or completely, as shown in FIG. 6). The interior of anterior portion 221 of frame 220 comprises a cylindrical bore 227 which extends inwardly away from anterior surface 238 of frame 220 (see FIG. 9). The interior of anterior portion 221 of frame 220 may be configured in the same manner as shown in FIG. 2 in order that lens 260 may be positioned and retained within the housing. In the embodiment shown in FIG. 6, however, housing 220 is configured such that an O-ring 280 may be positioned about the circumference of lens 260, rather than compressed against the posterior surface of the lens (as is the case in the embodiment shown in FIG. 1).

In order to assist in sealing air space 249 located between lens element 260 and contact lens element 240, one or more sealing members may be provided between image forming lens 260 and frame 220. In the particular embodiment shown in FIG. 6, O-ring 280 is employed for this purpose. O-ring 280 will also help to ensure that lens 260 is properly positioned within the housing. It should be kept in mind, however, that various other sealing devices may similarly be used for this purpose, such as a gasket or other known type of sealing member.

In order to allow for proper sealing by O-ring 80, an annular groove or gland 235 extends around the interior circumference of anterior portion 221. Groove 235 should be appropriately sized and configured such that not only may an O-ring 280 be positioned therein, but also such that lens 260 may be inserted into anterior portion 221 with O-ring 280 extending about the outer circumference (or edge) of lens 260. Lens 260 will urge O-ring 280 into groove 235 such that O-ring 280 is deformed, thereby helping to seal air space 249.

Figure 7:
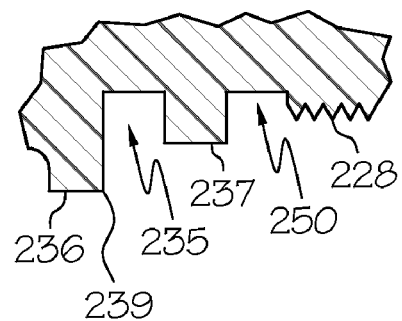
FIG. 7 is an enlarged cross-sectional view of a portion of the frame of FIG. 9.
Figure 9:
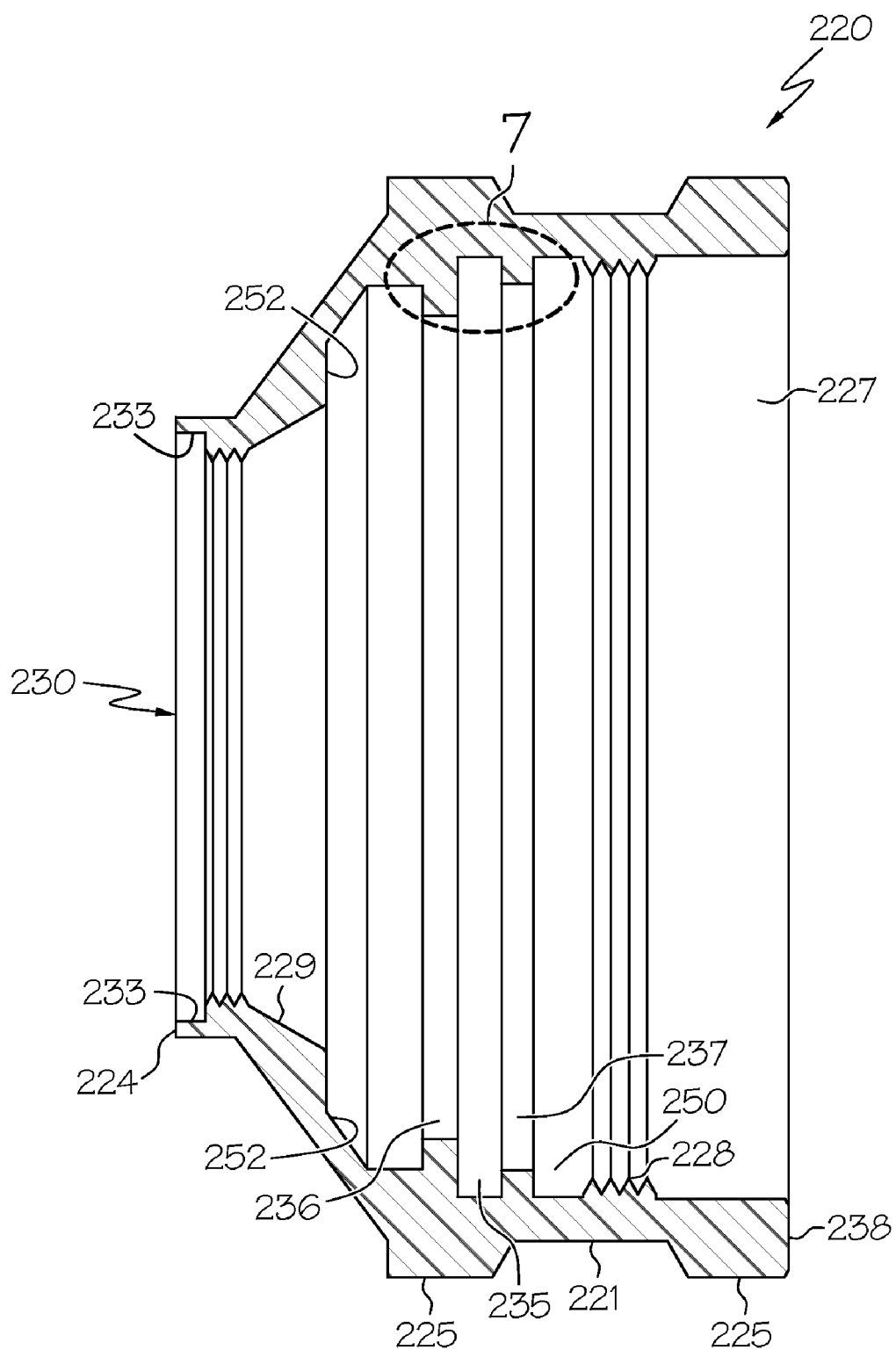
FIG. 9 is a cross-sectional view of the frame employed in the sterilizable ophthalmoscopy lens system of FIG. 6.

As best seen in FIGS. 7 and 9, groove 235 is provided by a pair of spaced-apart, radially-extending ridges 236 and 237 on the interior of cylindrical bore 227 (i.e., the interior of anterior portion 221). Groove 235 is located between ridges 236 and 237. Ridge 237 is located nearer to anterior surface 238 of housing 220 than is ridge 236. Stated differently, ridge 236 is located adjacent the posterior end of anterior portion 221 of housing 220. As best seen in FIG. 7, ridge 236 extends radially inward to a greater extent than ridge 237. In addition, ridge 237 is sized such that the inner diameter of cylindrical bore 227 at ridge 237 is slightly greater than the outer diameter of lens 260. In this manner, lens 260 may be inserted into housing 220, past ridge 237, and into the position shown in FIG. 6 (with the outer diameter of lens 260 compressing O-ring 280 into groove 235). Ridge 236, on the other hand, is configured such that the diameter of cylindrical bore 227 at ridge 236 is less than the outer diameter of lens 260. In this manner, the posterior surface of lens 260 will be positioned adjacent or even against edge 239 of ridge 236. Thus, ridge 236 will prevent lens 260 from being positioned too close to the contact lens element. As further discussed herein, a second groove 250 may be provided between ridge 237 and threaded portion 228 of cylindrical bore 227.

As was the case with the embodiment of FIG. 1, the interior wall of housing 220 may be tapered between anterior portion 221 and posterior portion 223. However, the embodiment of FIG. 6 includes an additional feature. In particular, the interior wall of housing 220 is tapered outwardly adjacent posterior portion 223, thus providing tapered wall portion 229. Tapered wall portion 229 also may taper outwardly at a smaller angle than the outer surface of frusto-conical portion 222, thus resulting in a gradual thickening of the wall of housing 220. However, tapered wall 299 does not extend all the way to anterior portion 221, as was the case in the embodiment of FIG. 1. Rather, a radially-extending wall 251 is provided between posterior portion 223 and anterior portion 221, as shown. In essence, wall 251 provides an annular shelf. A second tapered wall 252, which may be parallel to the outer wall of frusto-conical portion 222, then extends between wall 251 and anterior portion 221. As further discussed herein, a desiccant 253 may be applied to radially-extending wall 251.

Figure 8:
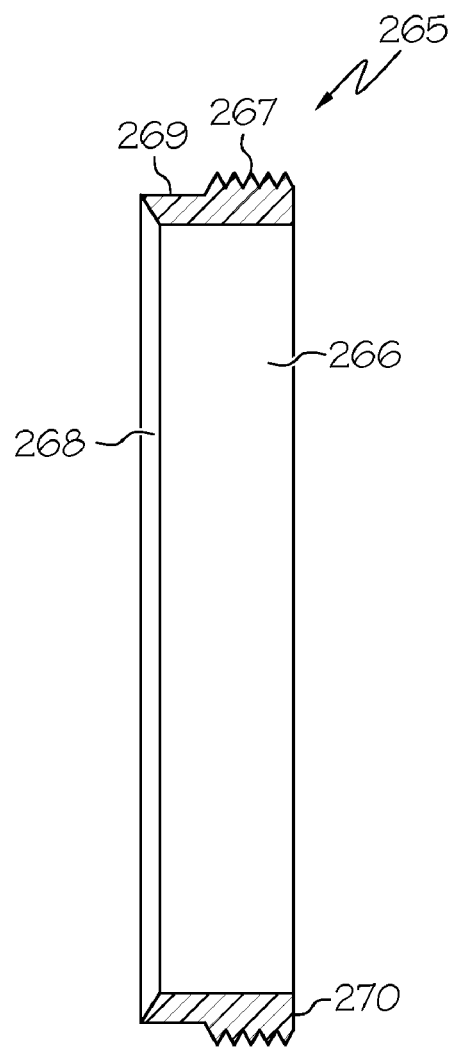
FIG. 8 is a cross-sectional view of the retaining ring employed in the sterilizable ophthalmoscopy lens system of FIG. 6.

Like the embodiment of FIG. 1, a retaining ring 265 may be employed to retain lens 260 within housing 220, as shown in FIG. 6. In particular, at least a portion of cylindrical bore 227 may be threaded, thus providing a threaded portion (or threads) 228. As best seen in FIG. 8, retaining ring 265 generally comprises a ring-shaped member having a central opening 266. The outer circumference of retaining ring 265 includes threads 267 configured to threadingly engage threads 228 of cylindrical bore 227 in frame 220. However, unlike the embodiment of FIG. 5, threads 267 do not extend along the entire length of the outer surface of retaining ring 265. Rather, retaining ring 265 includes an unthreaded posterior portion 269 having an outer diameter which is less than the outer diameter of threads 267. The outer diameter of unthreaded portion 269 may be slightly less than the interior diameter of anterior portion 221 of housing 220 at ridge 237, as best seen in FIG. 6. This will permit unthreaded portion 269 to advance past ridge 237 such that the posterior edge 268 of retaining ring 265 may be urged against the anterior surface of lens 260.

Posterior edge 268 which extends about the circumference of central opening 266 may be beveled in order to correspond to the shape of the anterior surface of lens 260. In this manner, after image forming lens 260 has been positioned within frame 220 in the manner shown in FIG. 6, retaining ring 265 may be rotatingly inserted into cylindrical bore 227 such that threads 267 on retaining ring 265 will threadingly engage threads 228 of frame 220. In order to facilitate threading of retaining ring 265 into the housing, one or more notches (not shown) may be provided in the anterior end wall 270 of retaining ring 265 such that a spanner wrench or other tool may be used to install the retaining ring in the housing. Beveled edge 268 of retaining ring 265 will be urged against the anterior surface of lens 260, thereby retaining lens 260 within frame 220, while central opening 266 of retaining ring 265 will allow light rays to pass therethrough. It should also be pointed out that, depending upon the shape of image forming lens 260, at least a portion of lens 260 may extend entirely through the thickness of central opening 266 of retaining ring 265 (as shown in FIG. 6). It will also be noted that the proximal surface of lens 260 may rest against edge 239 of ridge 236. As best seen in FIG. 6, when lens 260 and retaining ring 265 are installed in frame 220, O-ring 280 will be compressed not only against the outer diameter of lens 260, but also two or more walls of groove 235.

As best seen in FIG. 9, the interior of the posterior portion 223 of frame 220 comprises a cylindrical bore 230 which extends inwardly away from posterior end 224 of frame 220. Cylindrical bore 230 is threaded such that a contact lens element 240 may be threadeningly secured to frame 220, as further described herein.

As in the embodiment of FIG. 1, contact lens element lens 240 includes a concave posterior surface 241 and a convex anterior surface 242. In order to facilitate positioning of lens 210 within a suture-down ring or other holding device, an annular surface 246 may extend about the circumference of concave posterior surface 241 of contact lens element 240.

Threads 244 extend about the circumference of contact lens element 240 and are located posterior to convex anterior surface 242. Threads 244 are spaced inwardly with respect to annular surface 246 such that the diameter of threads 244 is less than that of the outer diameter of contact lens element 240. In this manner, a flat surface 245 will be provided adjacent to threads 244 such that, when contact lens element 240 is threaded onto frame 220, flat surface 245 will engage the posterior end surface 224 of frame 220 (as seen in FIG. 6). Various methods may be used to provide a seal between contact lens element 240 and frame 220. For example, a gasket or other sealing member may be positioned (and compressed) between flat surface 245 of contact lens element 240 and posterior end surface 224 of frame 220. Alternatively, the sealing member arrangement of FIG. 1 may be employed, with suitable modification of contact lens element 240 and housing 220.

In the embodiment of FIG. 6, an alternative sealing arrangement is used. In particular, a groove (or chamber) 233 extends around the circumference of the posterior end surface 224 of the housing. Although groove or chamber 233 may have any of a variety of configurations, in the particular embodiment of FIGS. 6 and 9, groove 233 extends radially outwardly away from the inner wall of posterior portion 223 and axially inwardly away from posterior end surface 224.

Any of a variety of sealing members may be positioned within groove 233 in order to seal the contact lens element 240 to the frame, such as an O-ring or gasket. Alternatively, the sealing member may comprise a high temperature resistant sealant composition applied within groove 233. For example, a sealant such as a high temperature silicone sealant may be applied to the contact lens element and/or the groove 233. In particular, the sealant may be applied as a uniform bead on flat surface 245 of contact lens element 240. When the contact lens element is then threaded into housing 220, the sealant composition will fill groove 233 in order to provide a waterproof seal between the contact lens element and the housing. Some of the sealant composition may even migrate to between the mating threads of the contact lens element and the housing. If necessary, the sealant composition may be cured after assembly of the contact lens element and housing, in accordance with the directions provided by the manufacture of the sealant composition. The sealant should be resistant to high temperatures even in the presence of water vapor (i.e., autoclavable), maintain its flexibility over a wide temperature range (e.g., from ambient to autoclave temperatures), remain waterproof even during autoclaving, and be resistant to bleach, acid and alkali (sterilent-resistance). One particular sealant composition which may be used in the present invention is Sealant 736, available from Dow Corning. After curing, it may also be necessary to remove excess sealant which is dispelled from the interface between the contact lens element and the housing.

As mentioned previously, a second groove 250 is provided between ridge 237 and threaded portion 228 on the interior of anterior portion 221 of frame 220 (see FIG. 7). As seen in FIG. 6, when retaining ring 265 is threaded into the interior of frame 220, a channel having a rectangular cross-sectional shape will extend about the interior circumference of the frame between groove 250 and unthreaded posterior portion 269 of retaining ring 265. A sealing member may be positioned within this channel, such as an O-ring or gasket. For example, an O-ring may be compressed between the between groove 250 and unthreaded posterior portion 269 of retaining ring 265, thus providing a waterproof seal between retaining ring 265 and housing 220. This seal, coupled with the seal between the contact lens element and the housing, will ensure that air space 49 remains free of liquid (even after sterilization).

As an alternative to an O-ring or gasket, the sealing member in the channel described above may once again comprise a sealant composition. After the lens 260 has been positioned within the housing and inside O-ring 280, a sealant composition is applied to the junction of lens 260 and the housing. As the retaining ring 265 is threaded into the housing, the sealant composition will be urged around O-ring 280 within groove 235, into groove 250 and even between some of the mating threads on the retaining ring and the housing. Thereafter, the sealant composition may be cured, and excess sealant removed as needed.

In order to further ensure that air space 249 remains free of water and other fluids, a desiccant may be positioned within air space 249. By way of example, a desiccant composition 253 may be applied to one or more surfaces within air space 249, such as radially-extending wall 251. In order to apply the desiccant to the wall or other surface, an adhesive composition may be applied to the surface and thereafter desiccant particles or powder may be applied. Suitable desiccants include any substance(s) which has a high affinity for water, such as calcium oxide, calcium sulfate (Drierite) or silica gel. Any of a variety of high temperature adhesive compositions may be used, and even the sealant composition described previously may be used for this purpose.

Some sealant compositions may include volatile or oily components that may be deposited onto the lens surfaces within air space 249, particularly after repeated autoclaving. In order to prevent this, after lens system 210 has been partially assembled and the sealant cured, the entire assembly may be baked in order to drive off any volatiles or other oily components. For example, lens system 210 may be baked at 105° F. for about 12 hours. After baking, the assembly may be wiped and cleaned with a solvent.

The above-described lens may be sterilized in any of a variety of manners. For example, the lens assembly can be totally submersed in a liquid sterilant without risk of the sterilant leaking into air space 249. The lens assembly may also be sterilized in a steam environment at temperatures of at least 275° F. without water vapor leaking into air space 249. Thus, lens systems according to the present invention may be quickly and easily sterilized by any of a variety of methods.

The exemplary lens systems described above and shown in FIGS. 1–9 may be utilized for ophthalmoscopy lens systems intended for any of a variety of uses. Essentially, any multi-element ophthalmoscopy lens system in which air separates at least two of the elements may be configured in the manner described previously. Thus, multiple image forming lens elements may be included, as desired or necessary, and each of the image forming lens elements may be sealingly mounted to the housing in any of the manners described above.

When one of the lens elements comprises a contact lens element, as described previously, the shape of the surfaces of the contact lens element may be varied from that shown in order to provide the desired optical performance. The contact lens element may even include a flange, as well as suitable openings in the flange to accommodate surgical tools or instruments, as described in U.S. Pat. No. 5,963,301 (which is incorporated herein by reference). Such a lens system is particularly useful for vitroretinal surgery. A compound contact lens element may also be employed, as described, for example, in U.S. Pat. No. 5,523,810 (which is incorporated herein by reference).

Likewise, the image forming lens element may be configured to provide any desired optical performance and characteristics. In particular, the lens systems shown in FIGS. 1–9 are particularly useful as indirect ophthalmoscopy lenses. For example, the lens systems of U.S. Pat. No. 5,046,836 (which is incorporated herein by reference) may be readily modified in accordance with the teachings of the present invention in order to provide a sealed, sterilizable and auto-clavable lens system. The image forming lens also may be specifically configured for optimal viewing of certain structures or portions of the eye (e.g., the fundus). Thus, the present invention provides a sealed, sterilizable and auto-clavable lens system which may be adapted to any existing ophthalmoscopy lens designs in which an air space separates at least two of the elements of the lens.

Figure 10:
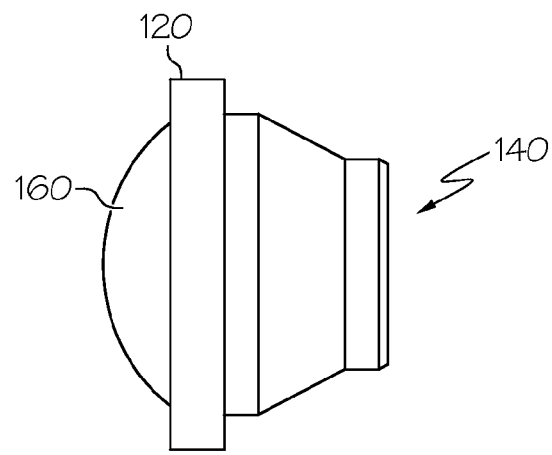
FIG. 10 is a side plan view of another embodiment of a sterilizable ophthalmoscopy lens system according to the present invention.

FIG. 10 depicts an alternative embodiment of a sterilent-resistant, autoclavable indirect ophthalmoscopy lens system. In fact, the embodiment of FIG. 10 is similar to the compound contact lens device shown in FIG. 7 of, and further described in, U.S. Pat. No. 5,523,810 ("the '810 patent, which is incorporated herein by way of reference). Using the terminology of the '810 patent, the lens system of FIG. 10 comprises a posterior lens portion 140 (i.e., a "contact lens element") and a biconvex anterior lens portion 160 (i.e., an "image forming lens") 160. Instead of being glued to one another as described in the '810 patent, contact lens element 140 and image forming lens 160, a frame or mounting ring 120 is employed.

As described previously, the glues typically used in configurations such as that described in the '810 patent are such that the lens system generally can only be sterilized using ethylene oxide. If autoclaving is attempted, the glue will hydrolize and eventually fail. In addition, differences in the thermal expansion of the materials (such as the plastic contact lens element and the glass imaging lens) will put additional stress on the glue bond. Cold sterilents (such as bleach) will also attack the glue chemically. If the two components of the lens system of FIG. 7 of the '810 patent separate due to glue failure, the optical function of the lens is altered and the lens becomes basically useless.

Contact lens element 140 can be easily machined from the plastic sterilent-resistant materials described previously. In fact, the use of these plastics does not substantially change the optical performance of the lens from that of the '810 patent. However, removing the glue has a more significant effect, as something should be used to optically match the two elements of the compound lens due to the difference in their refractive indices, and that substance needs to be easily inserted and removed for sterilization. Fluids are often used for such purposes, and optical modeling indicated that normal operating room saline solution, or even plain water, work well. Therefore, a thin layer of fluid (such as saline solution or even water) should be positioned between contact lens element 140 and image forming lens 160, thereby allowing the lens 160 to float with respect to contact lens element 140. Of course a fluid may be omitted if the mating surfaces are formed so as to optically match one another.

In order to maintain contact between contact lens element 140 and image forming lens 160 during use, while still allowing the two components to be separated from one another for sterilization purposes, a retaining ring 120 is employed. Retaining ring 120 maintains the two lens components in contact with one another without forcing the fluid layer out of the space between the two lens components. This fluid layer may be, for example, about 0.1 mm in thickness.

Figure 11:
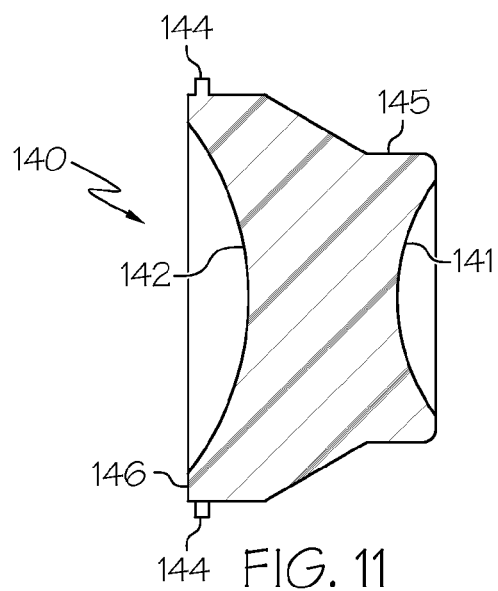
FIG. 11 is a cross-sectional view of the contact lens element of the sterilizable ophthalmoscopy lens system of FIG. 10.
Figure 12:
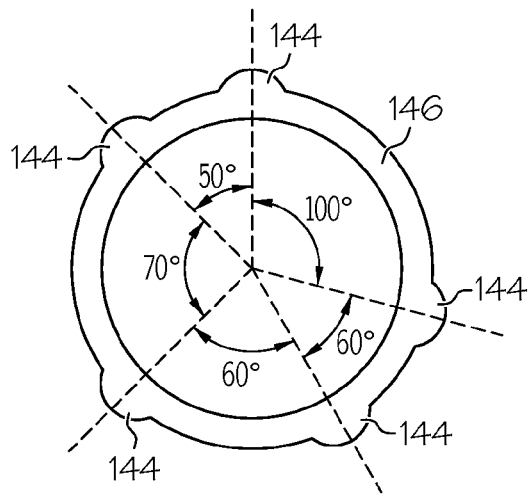
FIG. 12 is an end view of the contact lens element of the sterilizable ophthalmoscopy lens system of FIG. 10.

As best seen in FIGS. 11 and 12, contact lens element 140 includes a concave posterior surface 141 and a concave anterior surface 142. Concave posterior surface 141 has a shape substantially corresponding to the shape of an average cornea. By way of example, concave posterior surface 141 may be spherical or aspherical in shape and have an apical radius of approximately 7.5 to 8.0 mm. Concave anterior surface 142 has a shape corresponding to the posterior surface of lens 160 (as seen in FIG. 10). The shape of this surface, as well as the surface shapes of lens 160, may be varied in order to provide the desired imaging qualities.

Contact lens element 140 may have a cylindrical region 145 adjacent the posterior end of element 140, wherein cylindrical region 145 has a diameter suitable for use with a suture-down ring or other device for retaining the lens system on a patient's eye. Anterior end 146 of contact lens element 140 has a plurality of mounting tabs 144 which extend radially away from the exterior surface of contact lens element 140. In the embodiment shown, mounting tabs 140 are also spaced slightly away from anterior endwall 146 of contact lens element 140. Mounting tabs 140 are used to attach contact lens element 140 to retaining ring 120, in mating relation to lens element 160 (i.e., properly aligned, and with sufficient force to maintain alignment and prevent dislodgement, while not being so great of a force as to force out the fluid layer between the two lens elements).

Any number of a plurality of mounting tabs 144 may be spaced in a variety of patterns about contact lens element 140. However, applicant has found that at least three mounting tabs may be used, and better yet, four or even five. In addition, the mounting tabs may be spaced asymmetrically about contact lens element 140 such that the contact lens may be mounted to the retaining ring in a single rotational position. As shown in the end view of FIG. 12, the mounting tabs may be spaced about the circumference of the contact lens element such that they are spaced from one another by varying degrees, and the arrangement shown is merely exemplary of one possible arrangement. Also, in the embodiment shown, the mounting tabs are sufficiently spaced around the circumference of the contact lens element such that if one were to draw any diametrical line across the endwall (i.e., a line extending through the optical axis of the contact lens element) at least two mounting tabs would be positioned on either side of the diametrical line. Such a spacing will help to ensure that the two lens components will not be accidentally dislodged from alignment during use. It should also be pointed out that the shape of mounting tabs 144 is merely exemplary, and any shape which fits into the slots on the retaining ring (described below).

Figure 13:
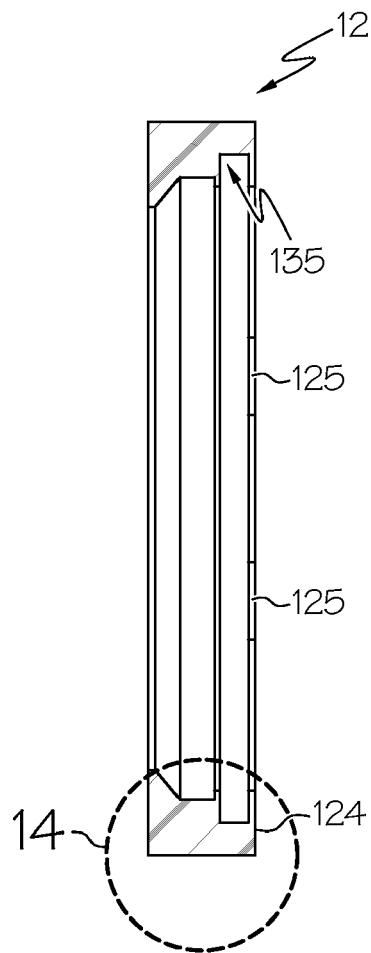
FIG. 13 is a cross-sectional view of the retaining ring of the sterilizable ophthalmoscopy lens system of FIG. 10.
Figure 14:
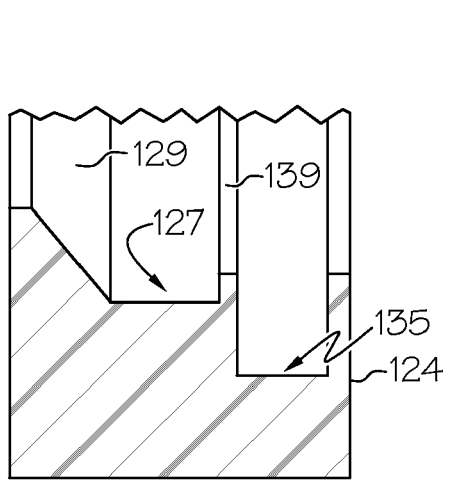
FIG. 14 is an enlarged cross-sectional view of a portion of the frame of FIG. 13.
Figure 15:
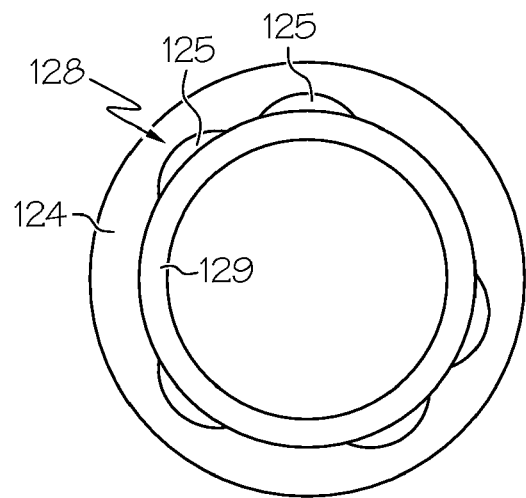
FIG. 15 is an end view of the retaining ring of FIG. 13.

As best seen in FIGS. 13–15, retaining ring 120 comprises an annular ring having an anterior groove 127 for accommodating biconvex lens element 160 and a posterior groove 135 which accommodates the mounting tabs 144 of the contact lens element. A circular flange 139 extends between these two grooves. Posterior endwall 124 of retaining ring 120 includes a series of slots (or notches) 125 which are spaced so as to correspond to the mounting tabs 144 of the contact lens element. The number, shape and size of the slots 125 should correspond to that of the mounting tabs 144, although the slots should be slightly larger. The semi-hemispherical shape of slots 125 depicted is merely exemplary of one possible arrangement. It should also be pointed out that the width of slot 135 may be slightly greater than the thickness of mounting tabs 144 in order to allow some lateral play between the contact lens element and the retaining ring. This will ensure that the contact lens element is not forced against lens 160 with so much force that the fluid layer therebetween is forced out.

Figure 16:
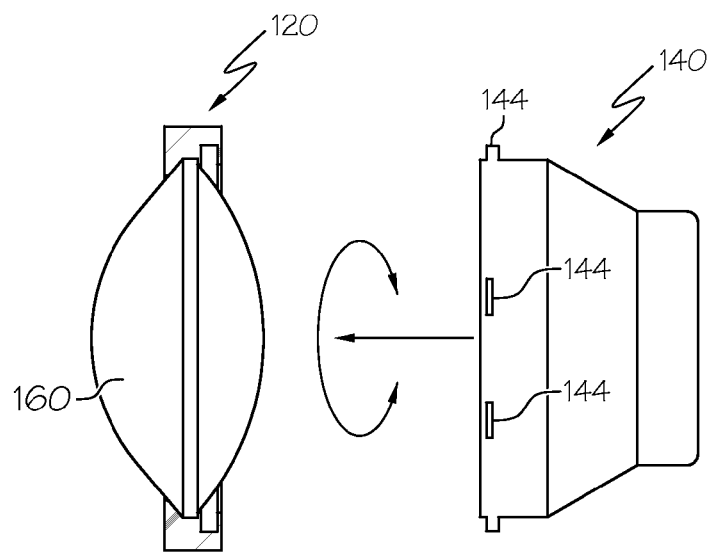
FIG. 16 is a side, partially cross-sectional view depicting the assembly of the sterilizable ophthalmoscopy lens system of FIG. 10.

Groove 127 has a tapered or beveled anterior wall 129 which may correspond to the shape of the anterior surface of lens 160. Groove 127 should also be sized and shaped such that it will firmly hold lens 160. In particular, since retaining ring 120 may be made from a sterilent-resistant and autoclavable plastic material such as Radel, retaining ring 120 will be somewhat flexible. In particular, retaining ring 120 may be configured such that lens 160 may be inserted through the posterior end of retaining ring 120 and snapped into place (as shown in FIG. 16). Flange 139 will flex slightly in order to allow lens 160 to be urged past flange 139 into groove 127 as shown. Once lens 10 is past flange 139, the flange will snap back, thereby locking lens 160 in groove 127 as shown in FIG. 16 (although lens 160 can be easily removed for purposes of sterilization). Once lens 160 has been locked into retaining ring 120, one or both of the mating surfaces of the contact lens element 140 and lens 160 are wetted with a fluid (such as saline). Thereafter, contact lens element 140 may be attached to retaining ring 120 (and thereby matingly aligned with lens 160) by inserting mounting tabs 140 into slots 125 at the proper location and rotating contact lens element 140 and/or retaining ring 120. Contact lens element 140 and/or retaining ring 120 may be rotated up to, for example, 180 degrees, such that it will require an additional 180 degrees of rotation to cause separation of the lens components (due to the asymmetrical arrangement of the mounting tabs).

For the lens system depicted in FIGS. 10–16, any of a variety of surface shapes may be employed for the contact lens element 140 and the imaging lens 160. By way of example, the following is a "prescription" for the various surfaces of a lens system according to an embodiment of the present invention, wherein contact lens element 140 is manufactured from a suitable plastic (e.g., Nightshield) and lens 160 from LAL59 glass:

| Surf | Radius | Thickness | Glass | Diameter | Conic Constant |
|---|---|---|---|---|---|
| Contact | 7.75 CV | 5.5 | PLASTIC | 10 | −0.18 |
| Interface | 7.091365 CV | 0.1 | TEARS | 16.3 | −3.062351 |
| Glass | 7.091365 CX | 7.293059 | LAL59 | 16.3 | −3.062351 |
|  | 9.286004 CX |  |  | 16.3 | −0.9719727 |

Figure 17:
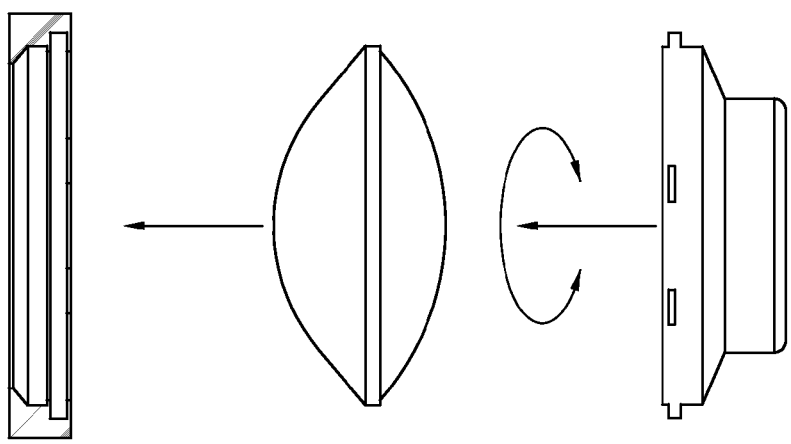
FIG. 17 is a side, partially cross-sectional view depicting the assembly of an alternative embodiment of a sterilizable ophthalmoscopy lens system.

FIG. 17 depicts an alternative design which provides a wider viewing angle. The prescription for such a lens may be as follows, wherein the same plastic is used for the contact lens element and LAH58 glass is used for lens 160:

| Surf | Radius | Thickness | Glass | Diameter | Conic Constant |
|---|---|---|---|---|---|
| Contact | 7.75 CV | 0.5 | PLASTIC | 10 | −0.18 |
| Interface | 5.872899 CV | 0.1 | TEARS | 16.3 | −2.974295 |
| Glass | 5.872899 CX | 8.5 | LAH58 | 16.3 | −2.974295 |
|  | 5.872899 CX | 6.306863 |  | 16.3 | −1.621825 |

What we claim is:

1. An ophthalmoscopy lens system, comprising:
 a contact lens element having a posterior lens surface with a concave shape substantially corresponding to the shape of an average cornea, and an anterior surface;
 an image forming lens element having anterior and posterior surfaces, wherein said posterior surface of said image forming lens element has a shape corresponding to the shape of the anterior surface of said contact lens element; and
 a retaining ring configured to maintain said contact lens element and said image forming lens element in a mating relationship with one another wherein said contact lens element and said image forming lens element are maintained in mating relationship with one another without the use of an adhesive agent therebetween.

2. The ophthalmoscopy lens system of claim 1, wherein said contact lens element and said image forming lens element are maintained in mating relationship with one another with a fluid layer located therebetween.

3. The ophthalmoscopy lens system of claim 1, wherein said retaining ring comprises an annular ring configured such that said retaining ring extends around the outer circumference of said image forming lens element, and further wherein said retaining ring is configured to engage said contact lens element so as to maintain the contact lens element and the image forming lens element in said mating relationship.

4. The ophthalmoscopy lens system of claim 3, wherein said retaining ring includes a groove extending about the interior circumference of said retaining ring, and further wherein said contact lens element includes a plurality of mounting tabs configured to be positioned within said groove for maintaining the contact lens element and the image forming lens element in said mating relationship.

5. The ophthalmoscopy lens system of claim 1, wherein said anterior surface of said contact lens element is concave, and said image forming lens element is biconvex.

* * * * *